(12) United States Patent
Cho

(10) Patent No.: US 10,307,228 B2
(45) Date of Patent: Jun. 4, 2019

(54) RETRACTOR FOR PERIODONTAL SURGERY

(71) Applicant: EBI Inc., Gyeongsan-si (KR)

(72) Inventor: Sang Choon Cho, New York, NY (US)

(73) Assignee: EBI Inc. (KR)

( * ) Notice: Subject to any disclaimer, the term of this patent is extended or adjusted under 35 U.S.C. 154(b) by 417 days.

(21) Appl. No.: 15/022,502

(22) PCT Filed: Aug. 25, 2014

(86) PCT No.: PCT/KR2014/007855
§ 371 (c)(1),
(2) Date: Mar. 16, 2016

(87) PCT Pub. No.: WO2015/037838
PCT Pub. Date: Mar. 19, 2015

(65) Prior Publication Data
US 2016/0228221 A1    Aug. 11, 2016

(30) Foreign Application Priority Data

Sep. 16, 2013  (KR) .......................... 10-2013-0111190

(51) Int. Cl.
*A61C 3/00* (2006.01)
*A61C 9/00* (2006.01)
*A61B 17/02* (2006.01)
*A61C 1/12* (2006.01)

(52) U.S. Cl.
CPC ............ *A61C 9/0033* (2013.01); *A61B 17/02* (2013.01); *A61C 1/12* (2013.01); *A61C 3/00* (2013.01)

(58) Field of Classification Search
CPC .......... A61C 9/0033; A61C 1/14; A61C 1/147
USPC ............................ 433/141–145; 600/184–246
See application file for complete search history.

(56) References Cited

U.S. PATENT DOCUMENTS

| 4,854,867 | A | 8/1989 | Meinershagen |
| 5,388,989 | A * | 2/1995 | Kountis ................... A61C 3/10 433/141 |
| 2007/0031788 | A1 | 2/2007 | Chao |
| 2010/0062392 | A1 | 3/2010 | Latiolais |
| 2012/0021379 | A1 * | 1/2012 | Beach ...................... A61C 3/00 433/143 |

FOREIGN PATENT DOCUMENTS

JP         2009502441 A      1/2009

* cited by examiner

*Primary Examiner* — Matthew J Lawson
(74) *Attorney, Agent, or Firm* — St Onge Steward Johnston and Reens LLC

(57) ABSTRACT

A retractor for periodontal surgery includes an elongated handle from which extends a first connection portion and a second connection portion, with a blade extending from the second connection portion. The handle and the first connection portion are positioned at a first angle, the first connection portion and the second connection portion are positioned at a second angle. The first and second connection portions are generally co-planar. The blade is obliquely positioned at a third angle relative to the central axis of the second connection portion. The blade may be easily inserted into an incision in a patient's gum so as to retract the incision.

14 Claims, 4 Drawing Sheets

[Fig. 1]
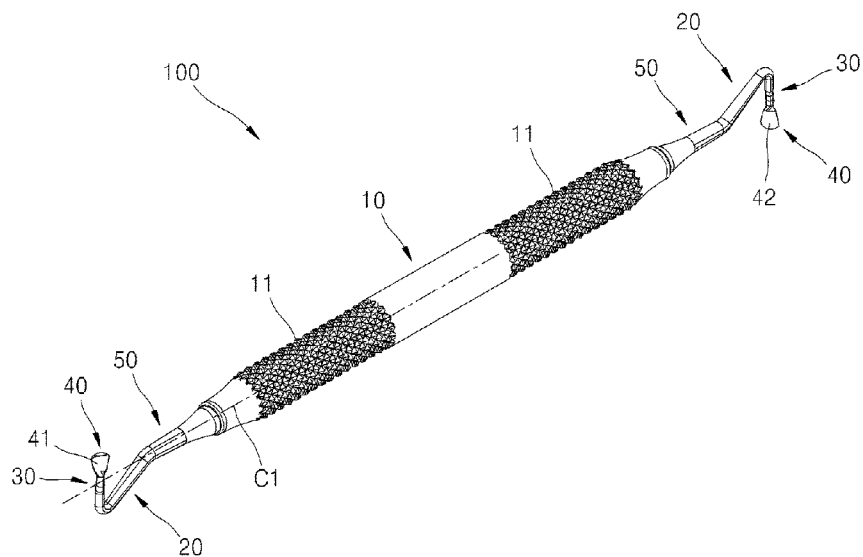
[Fig. 2]
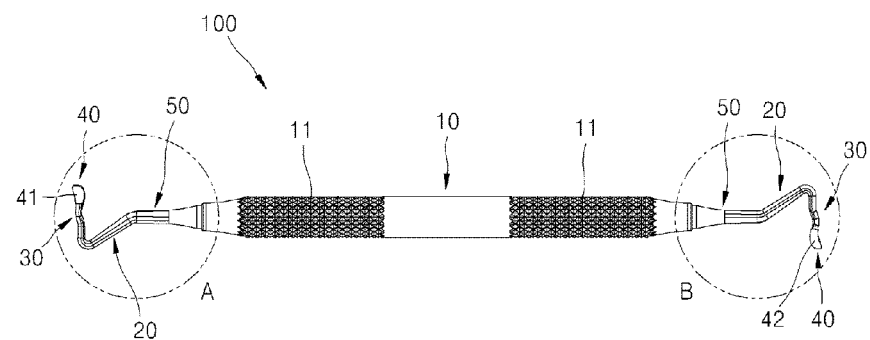
[Fig. 3]
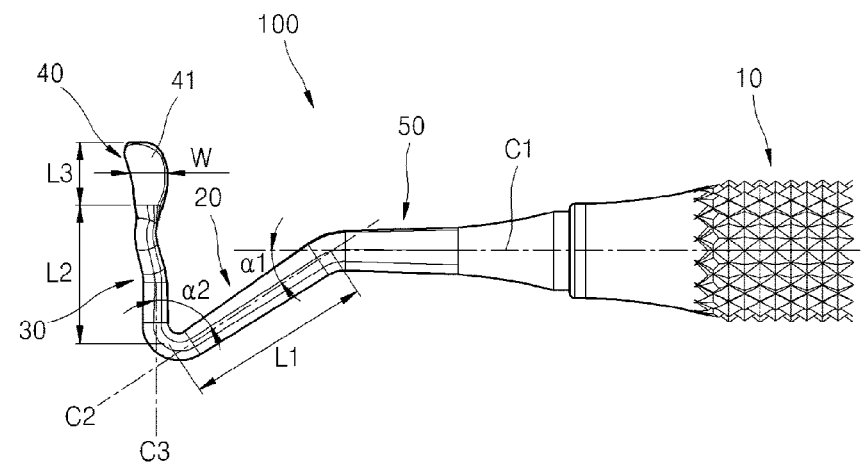

[Fig. 4]
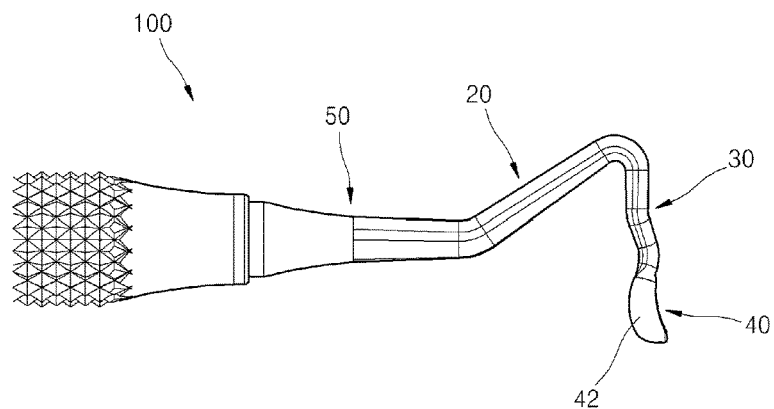
[Fig. 5]
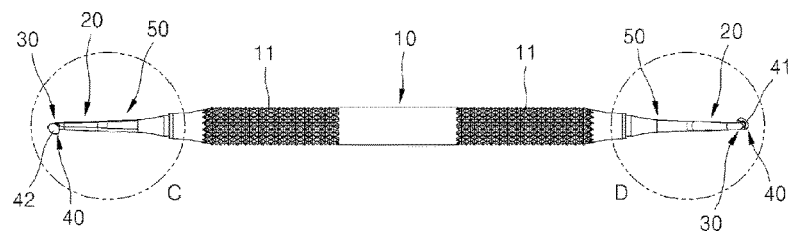
[Fig. 6]
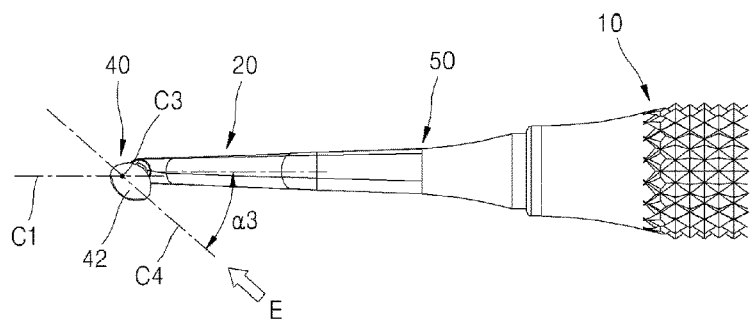
[Fig. 7]
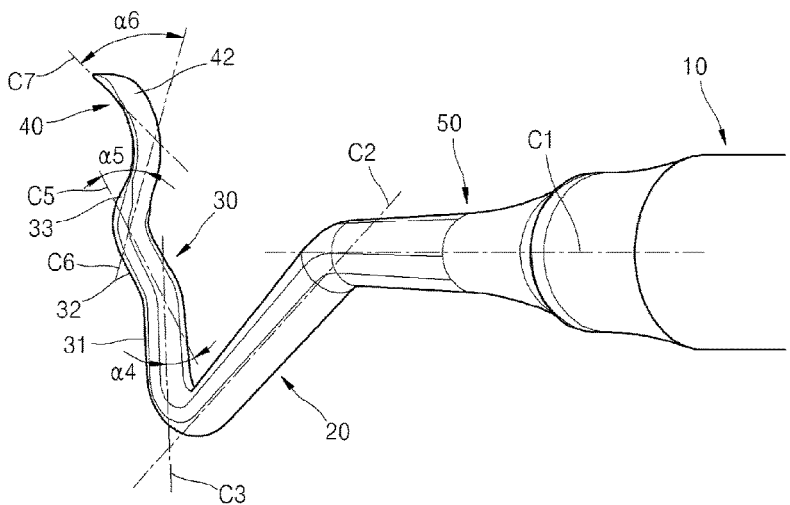

[Fig. 8]
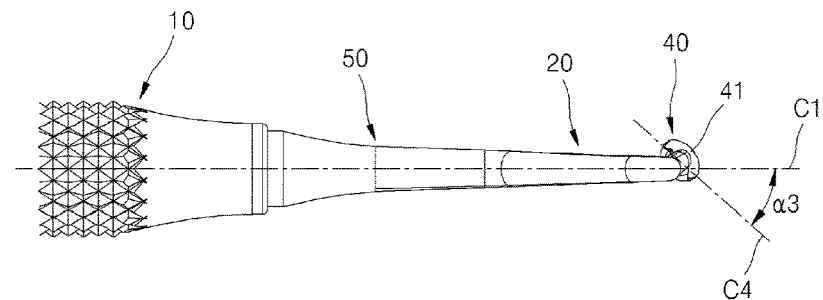
[Fig. 9]
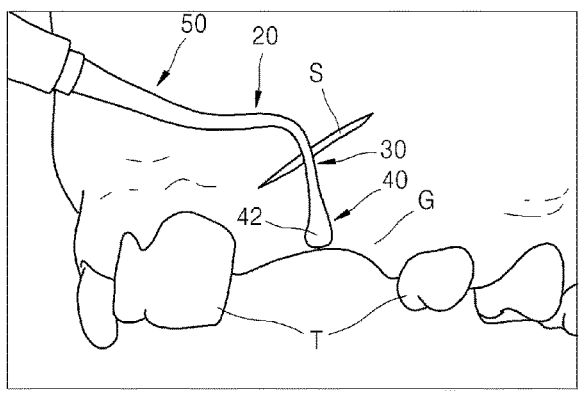
[Fig. 10]
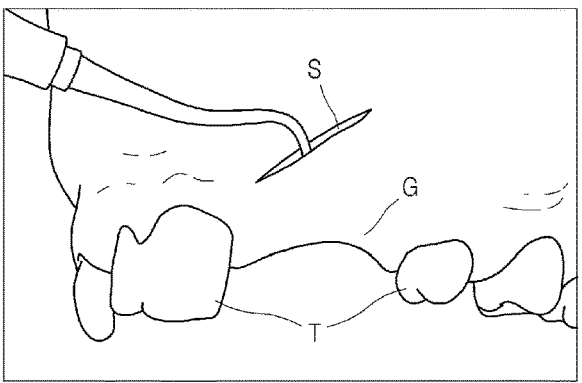
[Fig. 11]
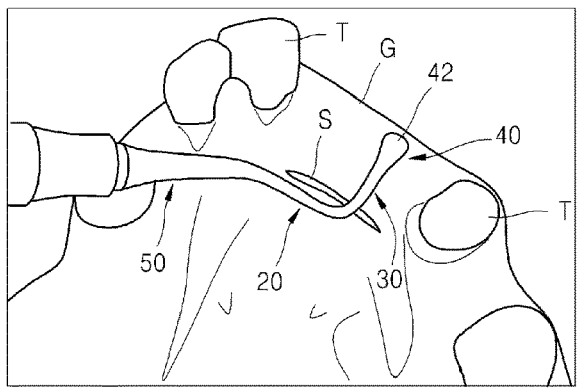

[Fig. 12]
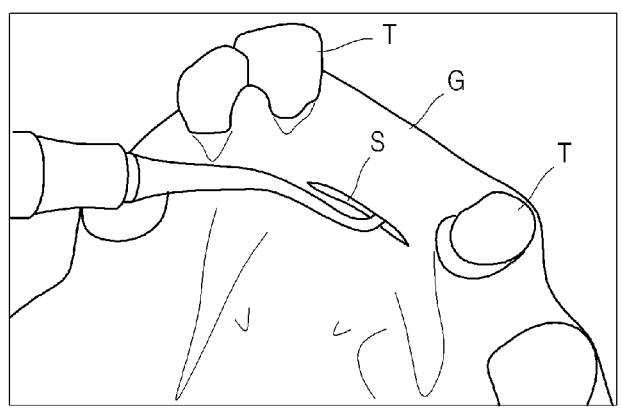

RETRACTOR FOR PERIODONTAL SURGERY

FIELD OF THE INVENTION

The present invention relates to a retractor for periodontal surgery, and more particularly, to a retractor for periodontal surgery, which may retract an opening in the gums by easily inserting a blade into the opening even in the circumstances including diverse oral cavity shapes or teeth alignments.

BACKGROUND OF THE INVENTION

Retractors for periodontal surgery are instruments used for periodontal surgery by being inserted into an opening in the gums to lift up or retract the opening. A retractor for periodontal surgery, which is a cylindrical member extending linearly long, generally includes a handle held by a user and a blade connected to at least one of opposite end portions of the handle and inserted into the opening.

In a retractor for periodontal surgery according to a related art, a connection structure between the blade and the handle generally has a linear shape or a simple hook shape. Accordingly, it is difficult to secure a work space in a mouth during surgery according to the position of an opening in the gums. Furthermore, individual characteristics of patients having diverse oral cavity shapes or teeth alignments may not be sufficiently reflected.

SUMMARY OF THE INVENTION

The present inventive concept provides a retractor for periodontal surgery, which has an improved structure to retract an opening in the gums by easily inserting a blade into the opening even in the circumstances where there are diverse oral cavity shapes or teeth alignments.

According to an aspect of the present inventive concept, there is provided a retractor for periodontal surgery, which is used to lift up or retract an opening in a gum by being inserted into the opening, the retractor including a handle having a long extended shape, a first connection portion comprising a first end portion and a second end portion, the first end portion of the first connection portion being connected to the handle, a second connection portion comprising a first end portion and a second end portion, the first end portion of the second connection portion being connected to the second end portion of the first connection portion, a blade connected to the second end portion of the second connection portion, in which the handle and the first end portion of the first connection portion form a preset first angle, the first end portion of the second connection portion and the second end portion of the first connection portion form a preset second angle, and the first connection portion, the second connection portion, and the handle are located on a same plane.

The preset first angle may be about 20° to about 40°.
The preset second angle may be about 60° to about 80°.
The first connection portion may linearly extend in a lengthwise direction.

A length of the first connection portion may be about 10 mm to about 12 mm.

A length of the second connection portion may be about 7 mm to about 9 mm.

A length of the blade may be about 5 mm to about 7 mm.
A width of the blade may be about 2.5 mm to about 3.5 mm.

The blade may be rotated by a preset third angle around a central axis of the second connection portion.

The third angle may be about 0° to about 10°.

The second connection portion may include a root portion comprising a first end portion connected to the second end portion of the first connection portion and a second end portion, a middle portion comprising a first end portion connected to the second end portion of the root portion and a second end portion, and an end portion comprising a first end portion connected to the second end portion of the middle portion and a second end portion.

The second end portion of the root portion and the first end portion of the middle portion may form a preset fourth angle, and the second end portion of the middle portion and the first end portion of the end portion may form a preset fifth angle.

The second connection portion may have a zigzag shape as the fourth angle is about 10° to about 30° and the fifth angle is about 20° to about 40°.

An edge of the blade may be circular or oval and the blade may have a scoop shape such that a lengthwise central axis of the blade is bent with a preset radius of curvature.

An end tip of the blade and the second end portion of the second connection portion may form a preset sixth angle.

The sixth angle may be about 30° to about 50°.

According to the present invention, since a retractor for periodontal surgery includes a first connection portion comprising a first end portion connected to the handle, a second connection portion comprising a first end portion connected to the second end portion of the first connection portion, and a blade connected to the second end portion of the second connection portion, in which the handle and the first end portion of the first connection portion form a preset first angle, the first end portion of the second connection portion and the second end portion of the first connection portion form a preset second angle, and the first connection portion, the second connection portion, and the handle are located on a same plane, the blade may be easily inserted into an opening of a gum so as to retract the opening even in the circumstances including diverse oral cavity shapes or teeth alignments.

BRIEF DESCRIPTION OF THE DRAWINGS

FIG. 1 is a perspective view of a retractor for periodontal surgery, according to an embodiment.

FIG. 2 is a front view of the retractor for periodontal surgery of FIG. 1.

FIG. 3 is an enlarged view of a portion A of the retractor for periodontal surgery of FIG. 2.

FIG. 4 is an enlarged view of a portion B of the retractor for periodontal surgery of FIG. 2.

FIG. 5 is a plan view of the retractor for periodontal surgery of FIG. 1.

FIG. 6 is an enlarged view of a portion C of the retractor for periodontal surgery of FIG. 5.

FIG. 7 is an enlarged view of the retractor for periodontal surgery of FIG. 6 in a direction E.

FIG. 8 is an enlarged view of a portion D of the retractor for periodontal surgery of FIG. 5.

FIG. 9 illustrates a method of retracting an opening formed in an upper-jaw labial surface by using the retractor for periodontal surgery of FIG. 1.

FIG. 10 illustrates a state in which a retractor for periodontal surgery is inserted into the opening illustrated in FIG. 9.

FIG. 11 illustrates a method of retracting an opening formed in an upper-jaw lingual surface by using the retractor for periodontal surgery of FIG. 1.

FIG. 12 illustrates a state in which the retractor for periodontal surgery is inserted into the opening illustrated in FIG. 11.

DETAILED DESCRIPTION OF THE INVENTION

Hereinafter, an embodiment of the present inventive concept is described in detail with reference to the accompanying drawings.

FIG. 1 is a perspective view of a retractor for periodontal surgery, according to an embodiment. FIG. 2 is a front view of the retractor for periodontal surgery of FIG. 1. FIG. 3 is an enlarged view of a portion A of the retractor for periodontal surgery of FIG. 2.

Referring to FIGS. 1 to 3, a retractor 100 for periodontal surgery according to the present embodiment is an instrument for periodontal surgery used to lift up or retract an incision or opening S of a gum G by being inserted into the opening S and may include a handle 10, a first connection portion 20, a second connection portion 30, and a blade 40.

The handle 10 is a cylindrical member linearly extending long along a first central axis C1 and is formed of a material including at least one of stainless steel, titanium, and titanium nitride, which are of a surgical operation level.

A grip portion 11 to prevent slipping of a users hand is formed on an outer circumferential surface of opposite end portions of the handle 10. In the present embodiment, the grip portion 11 includes a plurality of embossing protrusions.

The first connection portion 20 is a cylindrical portion linearly extending long along a second central axis C2 and has a first end portion that is connected to the handle 10. In the present embodiment, a length L1 of the first connection portion 20 is about 10 mm to about 12 mm.

The first central axis C1 of the handle 10 and the first end portion of the first connection portion 20 form a preset first angle α1, as illustrated in FIG. 3, and the first angle α1 has a value of about 20° to about 40°.

In the present embodiment, the first connection portion 20 is connected to the handle 10 via an extension portion 50 that linearly extends long from each of the opposite end portions of the handle 10 along the first central axis C1.

The extension portion 50 is a portion having a conic shape such that a diameter of the extension portion 50 gradually decreases toward the first connection portion 20.

The second connection portion 30 is a cylindrical portion extending long along a third central axis C3 and has a first end portion that is connected to a second end portion of the first connection portion 20. In the present embodiment, a length L2 of the second connection portion 30 is about 7 mm to about 9 mm.

The second connection portion 30 includes a root portion 31, a middle portion 32, and an end portion 33.

The root portion 31 is a cylindrical portion linearly extending a preset length along the third central axis C3 and has a first end portion that is connected to the second end portion of the first connection portion 20.

The first end portion of the root portion 31 and the second end portion of the first connection portion 20 form a preset second angle α2, as illustrated in FIG. 3, and the second angle α2 has a value of about 60° to about 80°.

The middle portion 32 is a cylindrical portion linearly extending a preset length along a fifth central axis C5 and has a first end portion that is connected to a second end portion of the root portion 31.

The second end portion of the root portion 31 and the first end portion of the middle portion 32 form a preset fourth angle α4, and the fourth angle α4 has a value of about 10° to about 30°.

The end portion 33 is a cylindrical portion linearly extending a preset length along a sixth central axis C6 and has a first end portion that is connected to a second end portion of the middle portion 32.

The second end portion of the middle portion 32 and the first end portion of the end portion 33 form a preset fifth angle α5, and the fifth angle α5 has a value of about 20° to about 40°.

As a result, the second connection portion 30 has a structure bent in a zigzag shape, as illustrated in FIG. 7.

The blade 40, which has an edge in a circular or oval shape, is a member having a scoop shape in which a lengthwise central axis (not shown) is bent with a preset radius of curvature, and has a lower end portion that is connected to a second end portion of the end portion 33.

Although the lower end portion of the blade 40 is parallel to the second end portion of the end portion 33, An end tip of an upper end portion of the blade 40 and the second end portion of the end portion 33 form a preset sixth angle α6, as illustrated in FIG. 7, and the sixth angle α6 has a value of about 30° to about 50°.

As illustrated in FIG. 3, a vertical length L3 of the blade 40 is about 5 mm to about 7 mm, whereas a horizontal width W of the blade 40 is about 2.5 mm to about 3.5 mm.

The blade 40 is obliquely rotated by a third angle α3 around the third central axis C3 the of the second connection portion 30, as illustrated in FIG. 6, and the third angle α3 has a value of about 0° to about 10°.

Each of the blades 40 arranged at the opposite end portions of the handle 10 is obliquely rotated clockwise by the third angle α3, as illustrated in FIGS. 6 and 8. Accordingly, when viewed by an observer located at the back of the sheet, the blade 40 at the right side in FIG. 8 is in a state of being rotated by the third angle α3 counterclockwise that is the opposite direction to the blade 40 at the left side.

In the present embodiment, the first connection portion 20, the second connection portion 30, the blade 40, the extension portion 50, and the handle 10 are located on one same plane.

The meaning of the "same plane" includes not only a concept of a mathematically perfect same plane, but also a concept of a substantially almost the same plane. In other words, in the present embodiment, the first central axis C1 of the handle 10, the second central axis C2 of the first connection portion 20, and the third central axis C3 of the root portion 31 are located on the same plane according to the concept of a mathematically perfect same plane, whereas the fifth central axis C5 of the middle portion 32 and the sixth central axis C6 of the end portion 33 are located on substantially the same plane with respect to the first, second, and third central axes C1, C2, and C3, though they are not located on the same plane according to the concept of a mathematically perfect same plane.

The values of the lengths L1, L2, and L3, the width W, and the angles α1, α2, α3, α4, α5, and α6 are determined through a plurality of clinical tests performed by the present inventor by taking into account the oral cavity shape or teeth alignment state of a typical patient.

In the following description, an example of a method of using the retractor 100 for periodontal surgery configured as above is described.

First, as illustrated in FIG. 9, the opening S is formed in an upper-jaw labial surface gum G. As the blade 40 of the retractor 100 for periodontal surgery is inserted into the opening S, as illustrated in FIG. 10, the opening S may be lifted up or retracted by using the retractor 100 for periodontal surgery. In this state, a direction in which a rear surface 42 of the blade 40 faces may be selected as necessary. In the present embodiment, the rear surface 42 of the blade 40 faces a labial surface.

As illustrated in FIG. 11, the retractor 100 for periodontal surgery may be used to retract the opening S formed in an upper-jaw lingual surface gum G. The opening S is formed in the upper-jaw lingual surface gum G, as illustrated in FIG. 11, and the blade 40 of the retractor 100 for periodontal surgery is inserted into the opening S, as illustrated in FIG. 12. Then, the opening S may be lifted up or retracted by using the retractor 100 for periodontal surgery. In this connection, which of the blades 40 formed at the opposite end portion of the retractor 100 for periodontal surgery is to be used may be determined according to the oral cavity shape or an alignment state of teeth T at a position where the opening S is located.

The operation method described with reference to FIGS. 9 to 12 may be easily used for an operation to reconstruct interproximal papilla that is a gum protrusion between the teeth T.

The retractor 100 for periodontal surgery configured as above may include the first connection portion 20 having the first end portion connected to the handle 10, the second connection portion 30 having the first end portion connected to the second end portion of the first connection portion 20, and the blade 40 connected to a second end portion of the second connection portion 30. The handle 10 and the first end portion of the first connection portion 20 form the preset first angle $\alpha 1$. A first end portion of the second connection portion 30 and the second end portion of the first connection portion 20 form the preset second angle $\alpha 2$. Since the first connection portion 20, the second connection portion 30, and the handle 10 are located on the same plane, the blade 40 may be easily inserted into the opening S of the gum G so as to retract the opening S even in the circumstances including diverse oral cavity shapes or teeth alignments.

Since, in the retractor 100 for periodontal surgery, the first angle $\alpha 1$ has a value of about 20° to about 40° and the second angle $\alpha 2$ has a value of about 60° to about 80°, the blade 40 may be easily inserted into the opening S formed at various positions in the gum G of the upper jaw or lower jaw.

Furthermore, since, in the retractor 100 for periodontal surgery, the first connection portion 20 linearly extends along a lengthwise direction, the length L1 of the first connection portion 20 is about 10 mm to about 12 mm, and the length L2 of the second connection portion 30 is about 7 mm to about 9 mm, the retractor 100 for periodontal surgery has a size suitable for an oral cavity structure of a typical patient.

Since, in the retractor 100 for periodontal surgery, the length L3 of the blade 40 is about 5 mm to about 7 mm and the width W of the blade 40 is about 2.5 mm to about 3.5 mm, the blade 40 may be easily inserted into an opening S having a relatively small length.

Furthermore, since, in the retractor 100 for periodontal surgery, the blade 40 is obliquely rotated by the preset third angle $\alpha 3$ around the third central axis C3 of the second connection portion 30, the blade 40 may be inserted into the opening S formed at various positions while held conveniently without excessive bending of a wrist.

Since, in the retractor 100 for periodontal surgery, the second connection portion 30 includes the root portion 31 having the first end portion connected to the second end portion of the first connection portion 20, the middle portion 32 having the first end portion connected to the second end portion of the root portion 31, and the end portion 33 having the first end portion connected to the second end portion of the middle portion 32, and the second end portion of the root portion 31 and the first end portion of the middle portion 32 form the preset fourth angle $\alpha 4$ and the second end portion of the middle portion 32 and the first end portion of the end portion 33 form the preset fifth angle $\alpha 5$, the second connection portion 30 having a zigzag bending shape, as illustrated in FIG. 7, may be formed. When the second connection portion 30 is formed in zigzag, an operation of inserting artificial bone (not shown) into the opening S is made easy and tissues of the gum G that are not used during the operation may be easily protected.

Furthermore, since, in the retractor 100 for periodontal surgery, an edge of the blade 40 is circular or oval and the blade 40 has a scoop shape such that the lengthwise central axis of the blade 40 is bent with a preset radius of curvature, when artificial bone is inserted into the opening S, the blade 40 may stably hold and fix the artificial bone.

Although, in the present embodiment, the method of performing an operation on an upper-jaw gum G using the retractor 100 for periodontal surgery is described above, an operation may be performed on a lower-jaw gum G by the same method.

The one or more embodiments described above are intended to exemplify the main concepts of the present inventive concept, and not limit the present inventive concept. It will be understood by one of ordinary skill in the art that various substitutions, amendments, or modifications may be made to the one or more embodiments of the present inventive concept without departing from the spirit and scope of the present inventive concept.

What is claimed is:

1. A retractor for periodontal surgery, which is used to lift up or retract an opening in a gum by being inserted into the opening, the retractor comprising:
    a handle having a long extended shape;
    a first connection portion comprising a first end portion and a second end portion, the first end portion of the first connection portion being connected to the handle;
    a second connection portion comprising a first end portion and a second end portion, the first end portion of the second connection portion being connected to the second end portion of the first connection portion;
    a blade connected to the second end portion of the second connection portion, wherein the handle and the first end portion of the first connection portion form a preset first angle, the preset first angle being about 20° to about 40°,
    the first end portion of the second connection portion and the second end portion of the first connection portion form a preset second angle, the preset second angle being about 60° to about 80°, and
    the first connection portion, the second connection portion, and the handle are located entirely on a same plane.

2. The retractor for periodontal surgery of claim 1, wherein the first connection portion linearly extends in a lengthwise direction.

3. The retractor for periodontal surgery of claim 1, wherein a length of the first connection portion is about 10 mm to about 12 mm.

4. The retractor for periodontal surgery of claim 1, wherein a length of the second connection portion is about 7 mm to about 9 mm.

5. The retractor for periodontal surgery of claim 1, wherein a length of the blade is about 5 mm to about 7 mm.

6. The retractor for periodontal surgery of claim 1, wherein a width of the blade is about 2.5 mm to about 3.5 mm.

7. The retractor for periodontal surgery of claim 1, wherein the blade is rotated by a preset third angle around a central axis of the second connection portion.

8. The retractor for periodontal surgery of claim 7, wherein the third angle is about 0° to about 10°.

9. The retractor for periodontal surgery of claim 1, wherein the second connection portion comprises:
 a root portion comprising a first end portion connected to the second end portion of the first connection portion and a second end portion;
 a middle portion comprising a first end portion connected to the second end portion of the root portion and a second end portion; and
 an end portion comprising a first end portion connected to the second end portion of the middle portion and a second end portion.

10. The retractor for periodontal surgery of claim 9, wherein the second end portion of the root portion and the first end portion of the middle portion form a preset fourth angle, and
 the second end portion of the middle portion and the first end portion of the end portion form a preset fifth angle.

11. The retractor for periodontal surgery of claim 10, wherein the second connection portion has a zigzag shape as the fourth angle is about 10° to about 30° and the fifth angle is about 20° to about 40°.

12. The retractor for periodontal surgery of claim 1, wherein an edge of the blade is circular or oval and the blade has a scoop shape such that a lengthwise central axis of the blade is bent with a preset radius of curvature.

13. The retractor for periodontal surgery of claim 12, wherein an end tip of the blade and the second end portion of the second connection portion form a preset sixth angle.

14. The retractor for periodontal surgery of claim 13, wherein the sixth angle is about 30° to about 50°.

\* \* \* \* \*